United States Patent
Nakano et al.

(10) Patent No.: US 7,283,614 B2
(45) Date of Patent: Oct. 16, 2007

(54) X-RAY DIAGNOSIS APPARATUS AND METHOD FOR CREATING IMAGE DATA

(75) Inventors: Shinichi Nakano, Utsonomiya (JP); Naoki Yamada, Nasu-Gun (JP); Tooru Takahashi, Otawara (JP); Masahiro Ozawa, Shioya-gun (JP); Kunitoshi Matsumoto, Minamisaitama-gun (JP); Yoshinori Shimizu, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/555,634

(22) Filed: Nov. 1, 2006

(65) Prior Publication Data

US 2007/0058781 A1   Mar. 15, 2007

Related U.S. Application Data

(63) Continuation of application No. 10/942,979, filed on Sep. 17, 2004, now abandoned.

(30) Foreign Application Priority Data

Sep. 19, 2003   (JP)   ............... P2003-328601

(51) Int. Cl.
*H05G 1/64*   (2006.01)

(52) U.S. Cl. .............. 378/98.12; 378/62; 382/130; 600/431

(58) Field of Classification Search .............. 378/4, 378/42, 62, 98.11, 98.12; 600/434, 431; 382/128, 130, 131, 132
See application file for complete search history.

(56) References Cited

U.S. PATENT DOCUMENTS 6,370,417 B1   4/2002   Horbaschek et al. ........ 600/424
6,577,889 B2   6/2003   Ichihashi .................... 600/425

*Primary Examiner*—Jurie Yun
(74) *Attorney, Agent, or Firm*—Oblon, Spivak, McClelland, Maier & Neustadt, P.C.

(57) ABSTRACT

An X-ray diagnosis apparatus and method for creating image data, wherein a plurality of sets of reference image data is created based on projection data obtained from a plurality of imaging directions to the object after an contrast agent is injected to an object, fluoroscopic image data are created based on projection data obtained from a desired imaging direction to the object, and fluoroscopic roadmap image data are created based on the fluoroscopic image data and reference image data whose imaging direction corresponds to the imaging direction of the fluoroscopic image data.

16 Claims, 13 Drawing Sheets

| IMAGING CONTDITION | IMAGE NUMBER | IMAGE TYPE | LAO (Degree) | CRA (Degree) |
|---|---|---|---|---|
| A-1 | 1-a | DSA | 15 | 0 |
| A-2 | 2-a | DSA | 15 | 15 |
| A-3 | 3-a | DSA | 15 | 30 |
| A-4 | 4-a | DSA | 30 | 0 |
| A-5 | 5-a | DSA | 30 | 15 |
| ⋮ | ⋮ | ⋮ | ⋮ | ⋮ |
| A-N | N-a | DSA | 45 | 45 |

FIG. 5

X-RAY DIAGNOSIS APPARATUS AND METHOD FOR CREATING IMAGE DATA

CROSS-REFERENCE TO RELATED APPLICATIONS

This application is a Continuation Application of an claims the benefit of priority under 35 U.S.C. §120 from U.S. application Ser. No. 10/942,979, filed Sep. 17, 2004 now abandoned, and claims the benefit of priority from prior Japanese Patent Application No. 2003-328601 filed on Sep. 19, 2003. The entire contents of each of the above applications are incorporated herein by reference.

FIELD OF THE INVENTION

The present invention relates generally to an X-ray diagnosis apparatus and method for creating image data.

BACKGROUND

A medical technology related to an X-ray diagnosis apparatus, an MRI apparatus and an X-ray CT apparatus becomes very important since 1970s when a computer technology improved.

A technology of an angio X-ray imaging is improving according to a development of catheter technique. In the angio X-ray imaging, an X-ray image, such as a cardiac image or an arteria/vein image of a whole body, is obtained when a contrast agent is injected into a blood vessel. An angio X-ray diagnosis apparatus generally includes an X-ray tube, an X-ray detector, a supporting unit which supports both the X-ray tube and the X-ray detector, a bed including a top plate and a signal processor, for example. The supporting unit, such as a C-arm or an Q-arm is applied with the bed which holds one side of the top plate. Thereby, the X-ray imaging from an appropriate imaging direction to a patient can be performed.

In the X-ray diagnosis apparatus which obtains the angio X-ray image, a fluoroscopic roadmap method is used, in order that the catheter is moved to an objective portion in the blood vessel. In the roadmap method, a first X-ray image data, referred as a reference image data below, is obtained from a predetermined imaging direction when the contrast agent is injected into the patient. Subsequently, a second image data, referred as a fluoroscopic image data, is obtained in real time from substantially the same predetermined imaging direction of the reference image data. The fluoroscopic image data and the reference image data are separately displayed or combined to be displayed. Thereby, the fluoroscopic roadmap image data is obtained.

In this case, a contrast image data which is obtained when the contrast is injected into the blood vessel is used as the reference image data, for example. Or a DSA (Digital Subtraction Angiography) image data where the blood vessel is mainly enhanced by performing a subtraction process between a mask image data which is obtained before the contrast agent is injected and the contrast image data may be used as the reference image data, instead.

In the fluoroscopic roadmap method, an imaging range of the reference image data is required to correspond to an imaging range of the fluoroscopic image data. However it is difficult to apply the fluoroscopic roadmap method, when the reference image data does not includes a position of a top of the catheter on the fluoroscopic image data, in other wards, the imaging range of the fluoroscopic image data is different from the imaging range of the reference image data.

In order to reduce the problem, the reference image data broader than the fluoroscopic image data is obtained in advance, and a partial reference image data which corresponds to the fluoroscopic image data is pull off from the boarder reference image data to be displayed according to movement of the C-arm, or the like. This method is described in Japanese Patent Disclosure (Kokai) No. 2000-342565, pp 4-6, FIGS. 1 and 2.

In order to set an imaging direction of the X-ray diagnosis apparatus including the C-arm, the handle, which can change the angle of the C-arm and is located on a console, is used. For instance, when the C-arm angle (Working Angle) is adjusted to obtain a coronary artery image, the followings are required, for example. (1) An objective blood vessel does not overlap another blood vessel on the image. (2) The X-ray is irradiated perpendicular to a direction along the blood vessel containing a diseased part, such as a stenosed part. (3) The X-ray is irradiated such that a flexion part can be easily observed. Due to these requirements, a doctor or a radiologist, referred as an operator below, carries out the X-ray imaging of the patient repeatedly, changing the angle of the C-arm, and observes the fluoroscopic image data on a monitor to set an appropriate imaging direction.

When the fluoroscopic roadmap image data is created from the reference image data which is obtained from the predetermined angle, the imaging direction of the fluoroscopic image data after the C-arm angle is changed is different from the imaging direction of the reference image data. Therefore, another reference image data corresponding to the fluoroscopic mage data in the imaging direction should be obtained. Due to the imaging of another reference image data, it is required that the contrast agent is injected again and the X-ray is irradiated to the patient, and efficiency of diagnosis and treatment is reduced.

SUMMARY

One object of the present invention is to ameliorate the above-mentioned problems. According to one aspect of the present invention, there is provided a An X-ray diagnosis apparatus, comprising:

an X-ray generating unit configured to irradiate an X-ray to an object;

an X-ray detector configured to detect the X-ray irradiated from the X-ray generating unit;

a reference image data creation unit configured to create a plurality of sets of reference image data based on projection data obtained from a plurality of imaging directions to the object after an contrast agent is injected to the object;

a fluoroscopic image data creation unit configured to create fluoroscopic image data based on projection data obtained from a desired imaging direction to the object; and a fluoroscopic roadmap image data creation unit configured to create fluoroscopic roadmap image data based on the fluoroscopic image data and reference image data whose imaging direction corresponds to the imaging direction of the fluoroscopic image data.

Also provided is a method for creating image data in an X-ray diagnosis apparatus, comprising creating a plurality of sets of reference image data based on projection data obtained from a plurality of imaging directions to the object after an contrast agent is injected to an object;

creating fluoroscopic image data based on projection data obtained from a desired imaging direction to the object; and creating fluoroscopic roadmap image data based on the fluoroscopic image data and reference image data whose imaging direction corresponds to the imaging direction of the fluoroscopic image data.

Also provided is An X-ray diagnosis apparatus, comprising:

an X-ray generating unit configured to irradiate an X-ray to an object;

an X-ray detector configured to detect the X-ray irradiated from the X-ray generating unit;

a subtraction image data creation unit configured to create subtraction image data from mask image data which is obtained before the contrast agent is injected into the object and contrast image data which is obtained after the contrast agent is injected into the object;

a catheter detection unit configured to detect a position of a catheter in the subtraction image data;

a blood vessel extraction unit configured to extract a blood vessel in the subtraction image data;

a pixel value change unit configured to change a pixel value of at least one pixel which is located on or near a top of the catheter and which is located in the blood vessel.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings:

FIG. 5 is a chart for setting a rotation angle of a C-arm in the first embodiment;

DETAILED DESCRIPTION OF EXEMPLARY EMBODIMENTS

Referring to FIGS, embodiments are explained.

In a first embodiment, an X-ray is irradiated from a plurality of imaging directions to a patient whom a contrast agent is injected to, and a plurality of sets of reference image data are obtained. From fluoroscopic image data which is obtained from a imaging data during a diagnosis or a treatment and a corresponding reference image data selected among the plurality of sets of the reference image data, a fluoroscopic roadmap image data is created.

Figure 1:
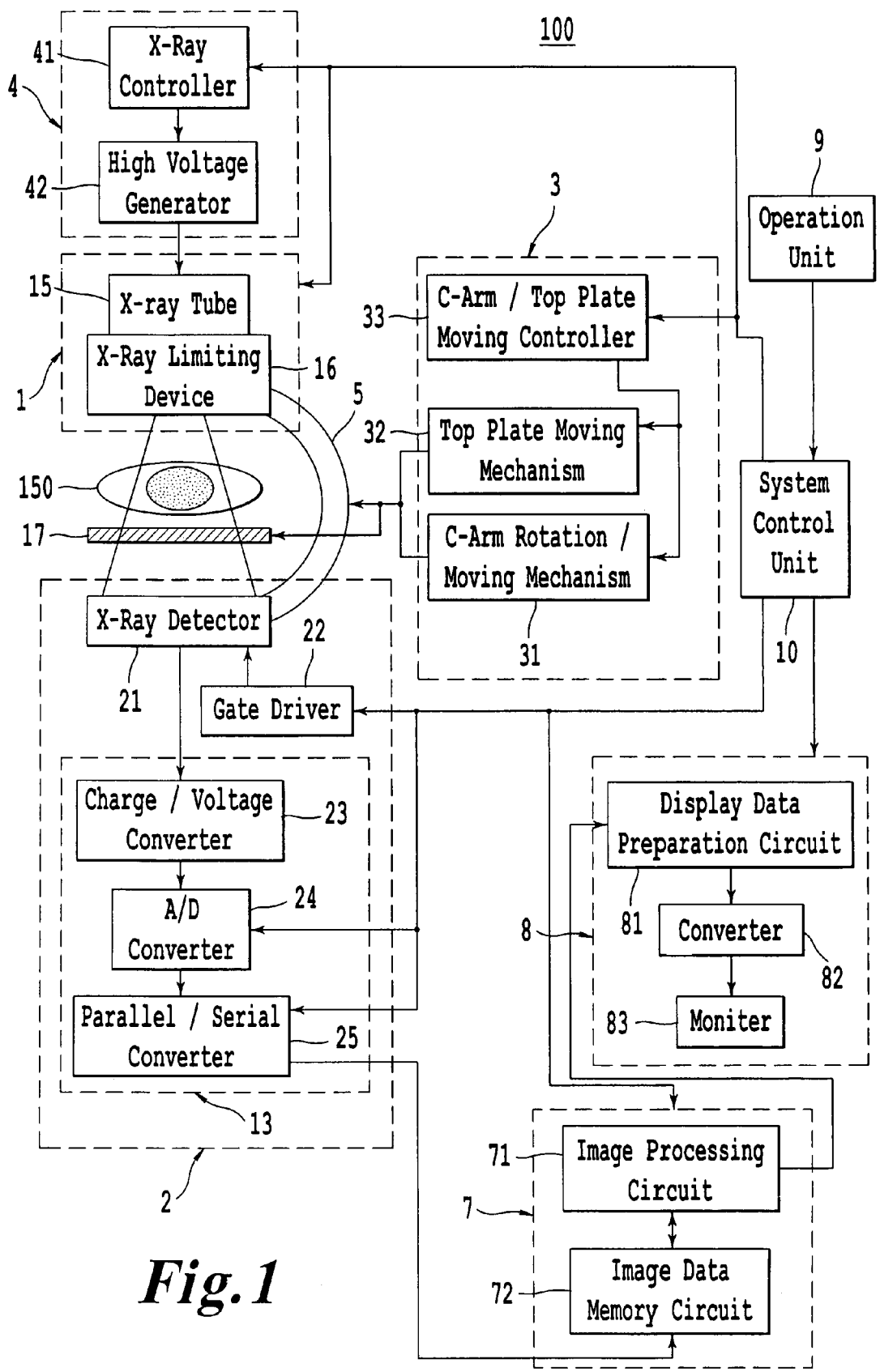
FIG. 1 is a block diagram of an X-ray diagnosis apparatus according to a first embodiment.
Figure 2:
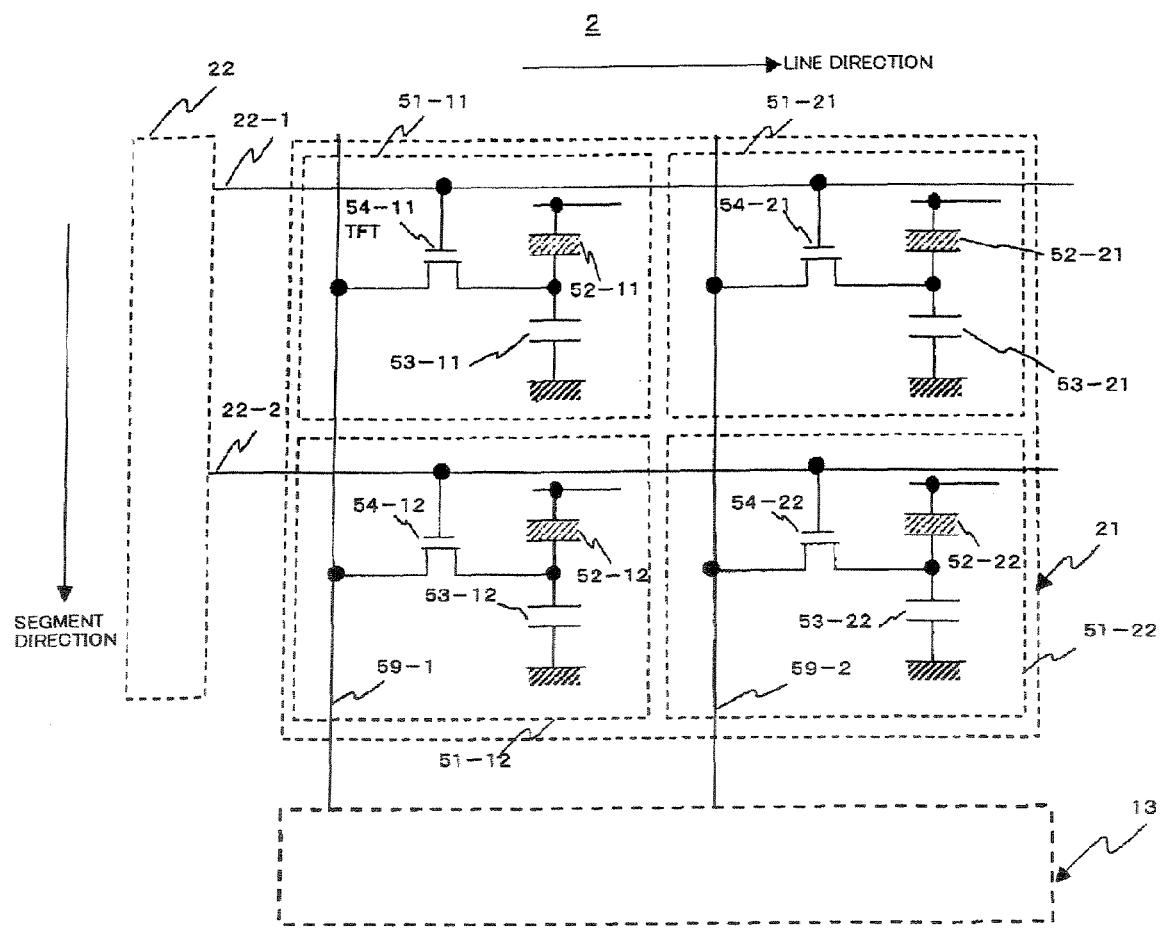
FIG. 2 is an illustration of an X-ray detector of the first embodiment.
Figure 3:
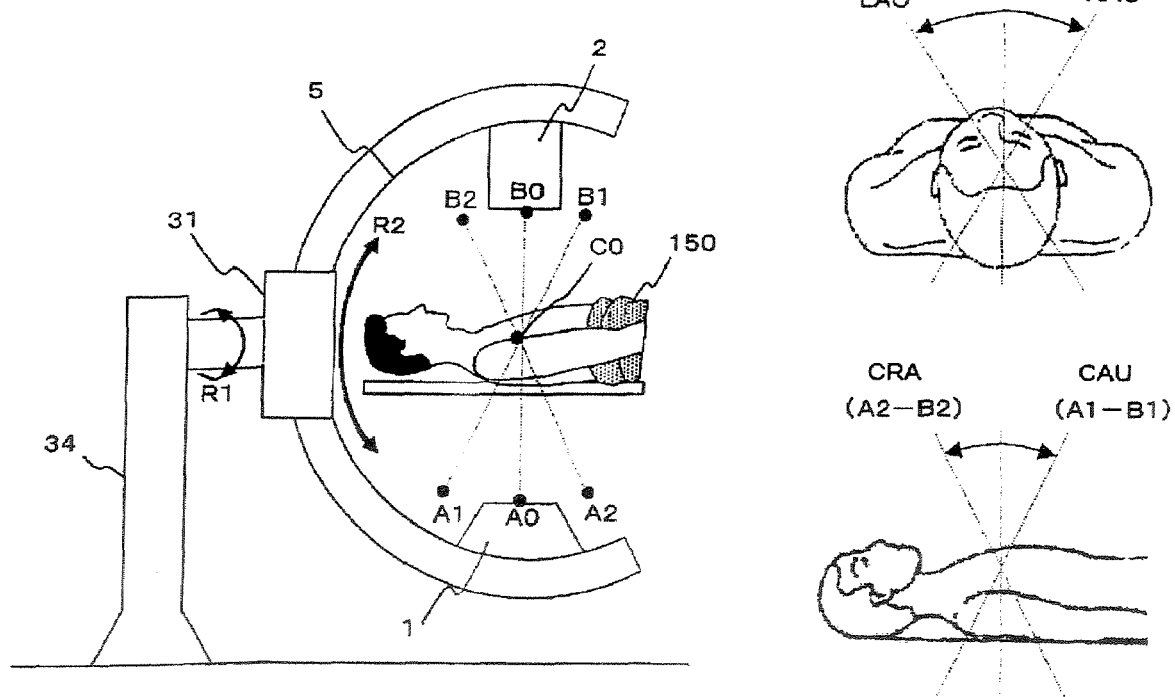
FIG. 3 is an illustration for explaining a rotation angle of an X-ray tube and the X-ray detector.

Referring to FIG. 1 through FIG. 3, a composition of an X-ray diagnosis apparatus is explained. FIG. 1 is a block diagram of the X-ray diagnosis apparatus, and FIG. 2 is an illustration of an X-ray detector.

The X-ray diagnosis apparatus 100 includes an X-ray irradiating unit 1 which irradiates the X-ray to the patient 150, the X-ray detecting unit 2 which detects the X-ray passing through the patient 150 to obtain two dimensional projection data, a C-arm 5 which supports the X-ray irradiating unit 1 and the X-ray detecting unit 2, a top plate 17 on which the patient 150 lies, and a high voltage generating unit 4 which generates high voltage which is required to irradiate the X-ray from the X-ray irradiating unit 1.

The X-ray diagnosis apparatus 100 further includes a moving unit 3 which moves the C-arm 5 and/or the top plate 17, an image processing unit 7, and a display unit 8. The image processing unit 7 obtains the reference image data and the fluoroscopic image data based on the projection data, creates the fluoroscopic roadmap image data, and stores these images. The display unit 8 displays a desired image data among the stored image data in the image processing unit 7.

The X-ray diagnosis apparatus 100 further includes an operation unit 9 and a system control unit 10. The operation unit 9 is used for selecting or inputting information, such as patient information, an imaging condition, a display condition related to the fluoroscopic roadmap display, and other commands. The system control unit 10 controls each unit in the X-ray diagnosis apparatus 100.

The X-ray irradiating unit 1 includes an X-ray tube 15 which generates the X-ray irradiated to the patient 150 and an X-ray limiting device which limits the X-ray generated in the X-ray tube 15 to form an X-ray cone beam. In the X-ray tube 15 which is a vacuum tube to generate the X-ray, an electron emitted from a cathode (filament) is accelerated and collided with a tungstic anode. The X-ray limiting device 16 is located between the X-ray tube 15 and the patient 150 and limits the X-ray beam irradiated from the X-ray tube 15 to a desired size of field.

As the X-ray detecting unit 2, a direct type X-ray detecting unit which directly converts the X-ray into an electric charge or a non-direct type X-ray detecting unit which converts the X-ray into a light and transform the light to an electric charge may be applied. The direct type X-ray detecting unit is mainly explained below, however both X-ray detecting units are applied alternatively. The X-ray detecting unit 2 includes an flat X-ray detector 21 which converts the X-ray passing through the patient 150 into the electric charge, a gate driver 22 which reads out the electric charge accumulated in the X-ray detector 21, and a projection data collecting unit 13 which collects a read out electric charge to obtain the projection data.

The flat X-ray detector 21 includes a plurality of small detecting elements which are 2-dimensionally arranged in a segment direction and a line direction as shown in FIG. 2. Each of the detecting elements includes a photoelectric film 52 which converts the irradiated X-ray into the electric charge according amount of the irradiated X-ray, a capacitor 53 which accumulate the electric charge, and a TFT 54 (Thin Film Transistor) which reads out the accumulated electric charge at a predetermined timing. A simplified case where the flat X-ray detector 21 includes 2×2 detecting elements which are arranged in the segment direction (up down direction in FIG. 2) and the line direction (right and left direction in FIG. 2) is explained below.

First terminals of photoelectric films 52-11, 52-12, 52-21 and 52-22 are connected to first terminals of capacitors 53-11, 53-12, 53-21 and 53-22, and the contact points are connected to source terminals of TFT 54-11, 54-12, 54-21 and 54-22, respectively. Second terminals of the photoelectric films 52-11, 52-12, 52-21 and 52-22 are connected to a bias power supply. Second terminals of the capacitors 53-11, 53-12, 53-21 and 53-22 are grounded. Gate terminals of the TFT 54-11 and 54-21 which are arranged in the line direction are commonly connected to output terminal 22-1 of the gate driver 22, and gate terminals of the TFT 54-12 and 54-22 are commonly connected to output terminal 22-2 of the gate driver 22.

Drain terminals of the TFT 54-11 and 54-12 which are arranged in the segment direction are commonly connected to a signal output line 59-1, and drain terminals of the TFT 54-21 and 54-22 are commonly connected to a signal output line 59-2. The signal lines 59-1 and 59-2 are connected to the projection data collecting unit 13. The gate driver 22 supplies driving pulses to the gate terminals of the TFT 54 in order that signal electric charges accumulated in the capacitors 53.

The projection data collecting unit 13 includes a charge/voltage converter 23 which converts the electric charges read out from the flat X-ray detector 21 to voltage signals, an A/D converter 24 which converts the voltage signals to digital signals and a parallel/serial converter 25 which converts the digital signals which are digitalized base on signals read out from the flat X-ray detector 21 by each line in parallel.

The moving unit 3 includes a top plate moving mechanism 32, a C-arm rotation/moving mechanism 31 and a C-arm/top plate moving controller 33. The top plate moving mechanism 32 linearly moves the top plate 17 with the patient 150 such that the X-ray irradiating unit 1 and the flat X-ray detector 21 are relatively moved to the patient 150. The C-arm rotation/moving mechanism 31 rotates the C-arm with the X-ray irradiating unit 1 and the X-ray detecting unit 2 around the patient 150 in a predetermined direction. The C-arm/top plate moving controller 33 controls the top plate moving mechanism 32 and the C-arm rotation/moving mechanism 31.

The C-arm/top plate moving controller 33 sets a magnification of an image, namely distance between a focus of the X-ray tube and the X-ray detector) based on a control signal from the system control unit 10. The C-arm/top plate moving controller 33 controls the C-arm rotation/moving mechanism 31 to set the rotation of the C-arm 5 and moving direction or moving amount or moving speed of the bed plate 17.

FIG. 3 is an illustration for explaining the rotati direction of the X-ray irradiating unit 1 and the X-ray detecting unit 2 controlled by the C-arm rotation/moving mechanism 31. In FIG. 3, the C-arm rotation/moving mechanism 31 is supported by a gantry 34 fixed on a floor such that the C-arm rotation/moving mechanism 31 is rotatable around a rotation axis along a body axis in R-1 direction. The C-arm 5 is supported by the C-arm rotation/moving mechanism 31 such that the C-arm 5 can slide in R-2 direction. On both sides of the C-arm 5, the X-ray irradiating unit 1 and the X-ray detecting unit 2 are provided.

The X-ray irradiating unit 1 and the X-ray detecting unit 2 rotate in a head direction (CRA) or a leg direction (CAU) by sliding the C-arm 5 in the R2 direction under a situation where the diseased part, such as a heart of the patient 150 corresponds to a rotation center axis (isocentre) CO of the X-ray beam. The X-ray irradiating unit 1 and the X-ray detecting unit 2 further rotate in a first incline (RAO) or a second incline (LAO) around the isocentre CO by rotating the C-arm 5 in the R1 direction under the situation. That is, the X-ray irradiating unit 1 and the X-ray detecting unit 2 rotate in the RAO, LAO, CRA and CAU according to the rotation of the C-arm 5. Thereby, it is possible to obtain the image from a desired direction.

The high voltage generating unit 4 shown in FIG. 1 includes a high voltage generator 42 which generates the high voltage between the anode and the cathode to accelerates the electron emitted from the cathode of the X-ray tube 15, and an X-ray controller 41 which controls an X-ray condition, such as a tube current, a tube voltage and an irradiating time, based on an instruction signal from the system control unit 10.

The image processing unit 7 includes an image processing circuit 71 which creates the fluoroscopic image data, the reference image data and the fluoroscopic roadmap image data to be displayed in a display unit 8. In the image processing circuit 71, several sorts of imaging processes are performed to the projection data which is obtained from the projection data collecting unit 13 to create a plurality of sets of the reference image data from several imaging directions and the fluoroscopic image data from a desired imaging direction. The fluoroscopic roadmap image data is created based on the fluoroscopic image data and the reference image data from the corresponding imaging direction to the fluoroscopic image data. Further, the image processing circuit 71 may have a function for creating DSA image data as the reference image data by performing a subtraction process on the mask image data and the contrast image data which are obtained before and after the contrast agent is injected, respectively.

The image processing unit 7 further includes an image data memory circuit 72 which stores the projection data, the reference image data, the fluoroscopic image data and the fluoroscopic roadmap image data.

The operation unit 9 is an interface device including an input device, such as a keyboard, a track ball, a joystick or a mouse, and a display panel, several switches, etc. The operation unit 9 is used for inputting the patient information, an imaging part (diseased part), the X-ray condition, the magnification of the image, the imaging condition, such as the imaging direction, or other commands, for example. The patient information may include an age, a sex, a body type, a region for imaging, an inspection method, and a result of a past diagnosis.

The display unit 8 is used for displaying the fluoroscopic image data, the reference image data or the fluoroscopic roadmap image data stored in the image data memory circuit 72. The display unit 8 includes a display data preparation circuit 81 which prepares display data containing the above mentioned image data and supplementary information, such as a number or a letter, a converter 82 which performs a D/A conversion process to the image data and the supplementary information and performs TV format conversion process to the D/A converted data to output picture signals, and a monitor 83, such as a LCD or a CRT, which displays the picture signals.

The system control unit 10 includes a CPU and a memory circuit. The system control unit 10 memorizes the information, such as the operation commands or the imaging condition supplied from the operation unit 9, and controls the whole units, such as the creation the projection data, the creation of the image data, or the movement of each unit.

Figure 4:
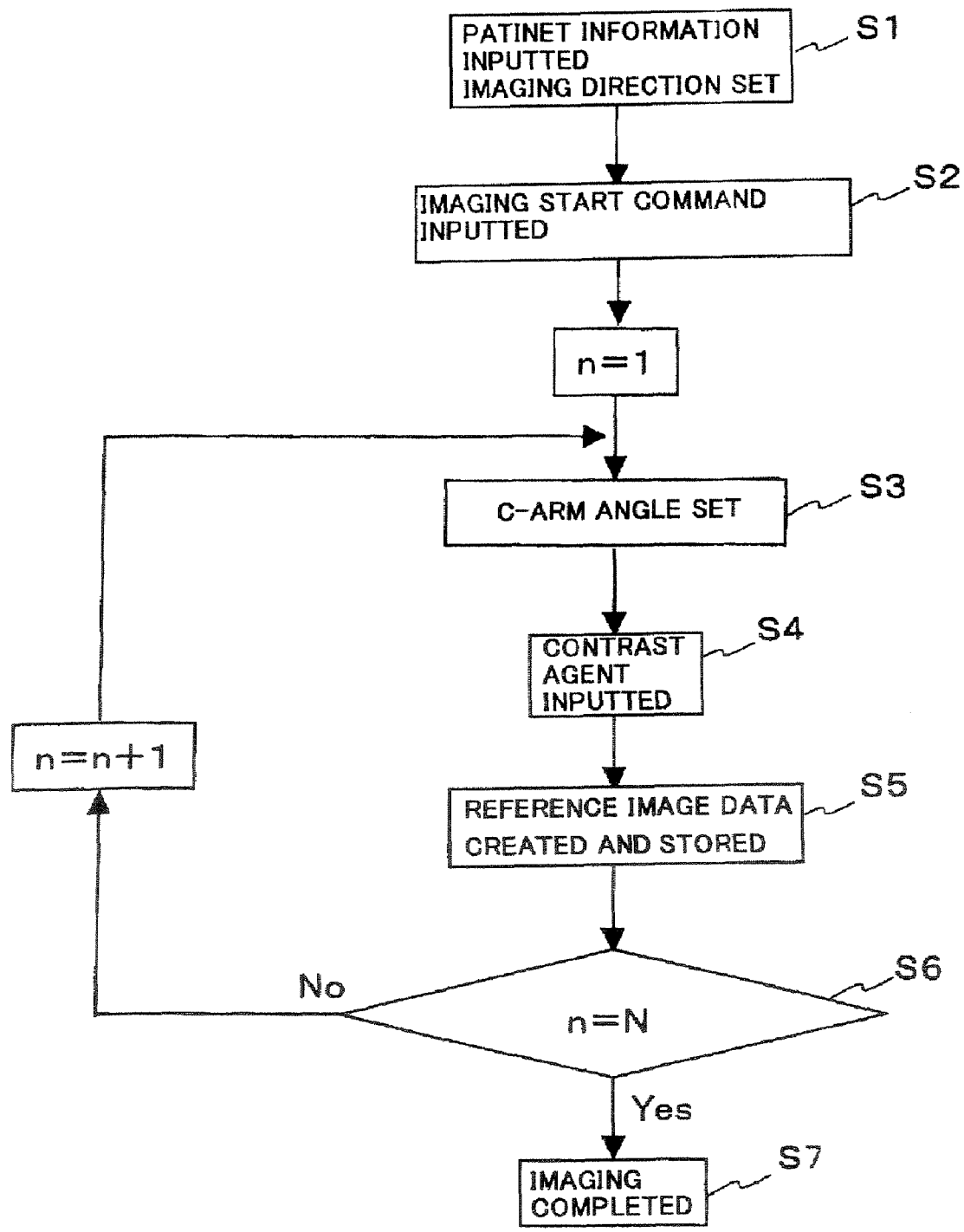
FIG. 4 is a flow chart for creating a reference image data in the first embodiment.
Figure 6:
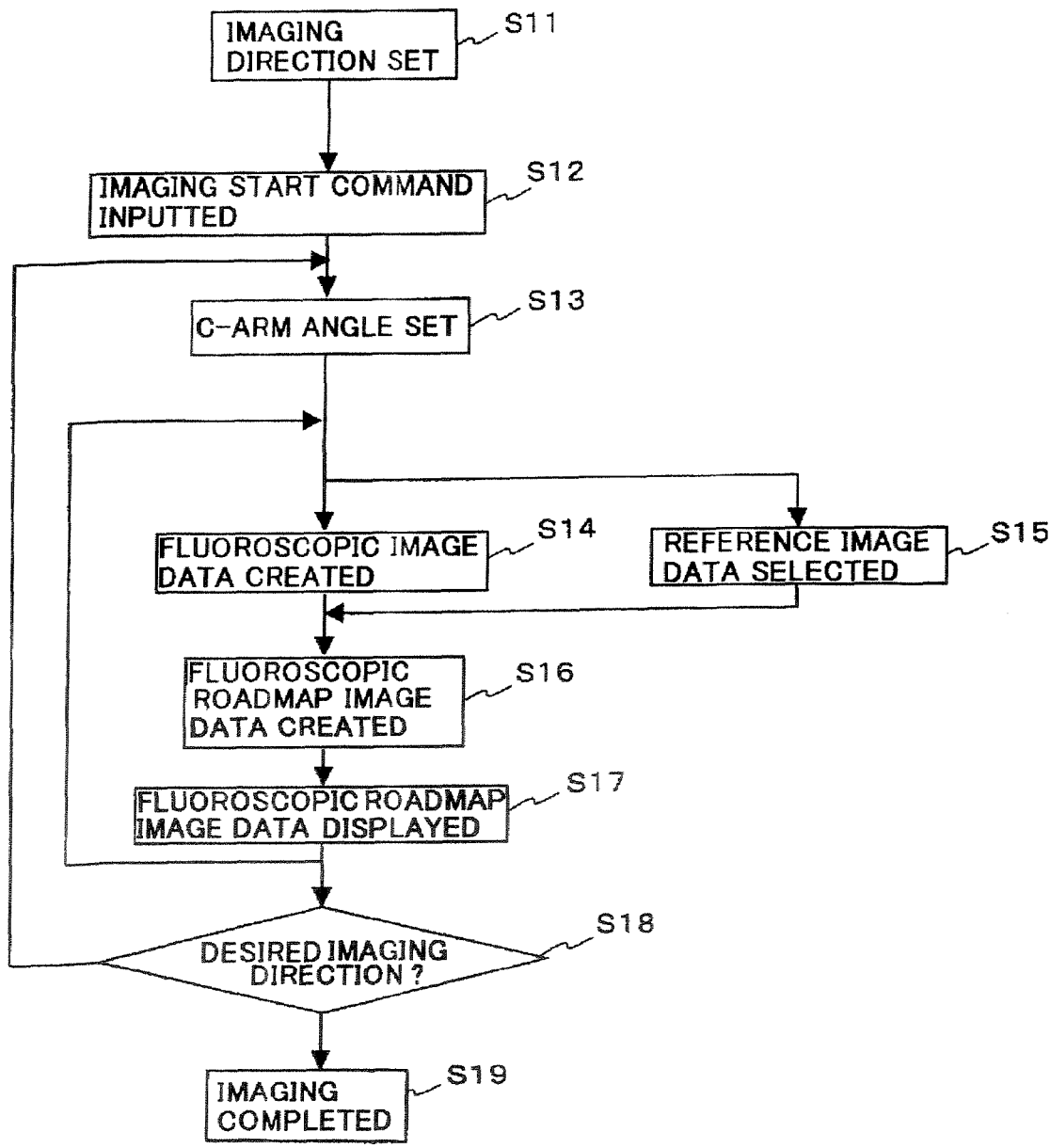
FIG. 6 is a flow chart for creating a fluoroscopic roadmap image data in the first embodiment.

An operation for creating the fluoroscopic image data in the X-ray diagnosis apparatus 100 is explained, referring to FIG. 1 through FIG. 8. In the flowcharts of FIG. 4 through FIG. 6, the following explanation mainly refers to a case where the coronary artery of the heart of the patient 150 is imaged or treated by the catheter, however an imaging or treatment part is not limited to the coronary artery.

When the X-ray diagnosis apparatus 100 turns ON, a server or a HIS (Hospital Information System) located in a hospital is electrically connected to the X-ray diagnosis apparatus 100 via a network. The operator inputs a patient ID with the operation unit 9, and the CPU in the system control unit 10 reads out the patient information or the imaging condition stored in a storage unit in the server or the HIS according to the patient ID, and memorizes the information in the memory circuit, and displays the information on the display panel of the operation unit 9.

The operator confirms the information displayed on the display panel and adjusts the information, if necessary. The imaging direction of the reference image data and the fluoroscopic image data from several imaging directions are set (Step S1).

In FIG. 5, the imaging direction is indicated. For instance, in a first imaging condition A-1, the imaging directions are 15 degrees in the LAO direction and 0 degree in the LAO direction. In a second imaging condition A-2, the imaging directions are 15 degrees in the LAO direction and 15 degrees in the CRA direction. Imaging conditions of A-3 through A-N are also determined, and these imaging conditions are memorized in the memory circuit of the system control unit 10.

After the imaging conditions are set, the operator inputs an imaging start command for creating the reference image data with the operation unit 9. The system control unit 10 receives the imaging start command, and the creation of the reference image starts (Step S2).

The system control unit 10 supplies the imaging direction information of the first imaging condition A-1 (n=1) memorized in the memory circuit to the C-arm/top plate moving controller 33. The C-arm/top plate moving controller 33 supplies a driving signal to the C-arm rotation/moving mechanism 31 based on the rotation angle of the C-arm 5 according to the imaging direction supplied from the system control unit 10. The imaging direction of the X-ray irradiating unit 1 and the X-ray detecting unit 2 attached to the C-arm 5 is set as 15 degrees in the LAO direction and 0 degree in the CRA direction (Step S3).

The contrast agent is injected from the catheter which is inserted into a vein of a inguinal region of the patient 150. The injection of the contrast agent may be manually performed by the operator who confirms that the set of the imaging direction is completed. Otherwise, the injection may be automatically performed by an injection unit based on an instruction signal supplied from the system control unit 10 (Step S4).

The system control unit 10 supplies a driving signal to the X-ray controller 41 to obtain the X-ray image data at the time when the contrast agent reaches the coronary artery. The X-ray controller 41 controls the high voltage generator 42 to supply the high voltage to the X-ray tube 15 based on a predetermined X-ray condition, and the X-ray tube 15 irradiates a pulsed X-ray via the X-ray limiting device 16 to the patient 150. The X-ray passing through the patient 150 is detected by the flat X-ray detector 21 located behind the patient 150.

The flat X-ray detector 21 includes a plurality of the detecting elements 51 arranged in the line direction and the segment direction as shown in FIG. 2. Each detecting element detects the X-ray passing through the patient 150, and accumulates the charge signal according to the amount of the X-ray in the capacitor 53. After the X-ray irradiation is completed, the gate driver 22 where a clock pulse is supplied from the system control unit 10 supplies the driving pulse to the flat X-ray detector 21. Thereby, the signal charges accumulated in the capacitors arranged in the line direction are sequentially outputted in the segment direction.

The outputted signal charges are converted to the voltage signals by the charge/voltage converter 23, and the output signals of the charge/voltage converter 23 are converted to the digital signals and then converted to projection data by the A/D converter 24 and the parallel/serial converter 25, respectively. The projection data is temporarily memorized in a memory in the parallel/serial converter 25. The system control unit 10 reads out the projection data in serial with respect to each line, and the read out data is stored in the image data memory circuit 72 as two dimensional projection data.

The image processing circuit 71 reads out the two dimensional projection data stored in the image data memory circuit 72, and creates the contrast image data by performing imaging process, such as edge enhancement or gray level correction. The contrast image data is stored in the image data memory circuit 72 as the reference image data (Step S5).

In the step of creating the reference image data, it is difficult to fill up the contrast agent in the entire desired part of the blood vessel at the same time in general, since the contrast agent flows out quickly from the desired part. In this reason, the X-rays are irradiated from the same angle several times in a predetermined period to the blood vessel where the contrast agent flows, and a plurality of sets of the contrast image data are obtained. An averaging process where the plurality of sets of the contrast image data are averaged, or a combination process where pixels which have large pixel values are combined may be performed. Thereby, a portion including the contrast agent may be displayed continuously.

After the creation of the reference image data according to the first imaging condition A-1 of the C-arm 5 is completed, the creation of the reference image data according to other imaging conditions A-2 (n=2) to A-N (n=N) is performed. The sets of the reference image data are stored in the image data memory circuit 72 (Step S3 and S6), and the creation of the reference image data is completed (Step S7).

The operator confirms the imaging condition of the fluoroscopic image data which is set by the operation unit 9. Subsequently, the operator selects or inputs at least one direction for the fluoroscopic image data. For instance, the operator may select the direction among the imaging conditions shown in FIG. 5, or may input the angle of the LAO or the CRA (Step S11).

The operator inserts the catheter from the vein of the inguinal region such that the position of the top of the catheter reaches the coronary artery, and inputs an imaging start command for creating the fluoroscopic image data and the fluoroscopic roadmap image data with the operation unit 9 (Step S12).

Based on the start command, the C-arm/top plate moving controller 33 receives the imaging condition, such as A-2, from the operation unit 9 via the system control unit 10. The C-arm/top plate moving controller 33 supplies the driving signal to the C-arm rotation/moving mechanism 31 according to the imaging condition, and the C-arm angle is set such that the imaging direction is 15 degrees in the LAO direction and 15 degrees in the CRA direction (Step S13). The system control unit 10 obtains the projection data and the fluoroscopic image data in the imaging direction. Since an operation for creating the fluoroscopic image data is the same as or similar to the operation for creating the reference image data, a detailed explanation is omitted.

As the operation described above, the image processing circuit 71 creates the fluoroscopic image data from the desired imaging direction (Step S14). The closet reference image data to the fluoroscopic image data in the imaging direction is selected and is read out among the plurality of sets of the reference image data stored in the image data memory circuit 72 (Step S15). The reference image data and the fluoroscopic image data are combined to create the fluoroscopic roadmap image data, the fluoroscopic roadmap image data is stored in the image data memory circuit 72 (Step S16).

The system control unit 10 reads out the X-ray image data stored in the image data memory circuit 72, and displays the X-ray image data on a monitor 83 of the display unit 8. That is, the system control unit 10 reads out the fluoroscopic roadmap image data stored in the image data memory circuit 72, and the display data preparation circuit 81 prepares the supplementary information, such as a number or a letter. The fluoroscopic roadmap image data and the supplementary information are combined and supplied to the converter 82. In the converter 82, the D/A conversion process and the TV format conversion process are performed, and the fluoroscopic roadmap image data which these processes are performed on is displayed on the monitor 83 (Step S17).

The operator proceeds the catheter and the Steps S14 to S17 are repeatedly executed. Thereby, the fluoroscopic roadmap image data from the desired direction is displayed on the monitor 83 in real time.

Figure 7:
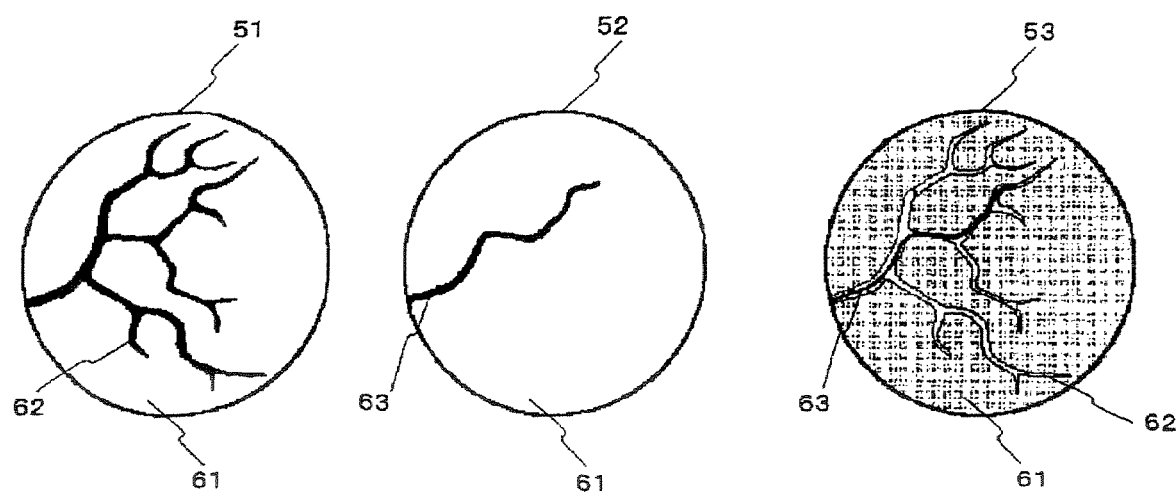
FIG. 7 is an illustration of a reference image data, a fluoroscopic image data and fluoroscopic roadmap image data.

FIG. 7 shows an illustration of the reference image data 51, the fluoroscopic image data 52 and the fluoroscopic roadmap image data 53 where the reference image data and the fluoroscopic image data are combined. The reference image data 51 mainly includes the image data of a soft tissue 61 and the blood vessel 62 where the contrast agent is injected. The fluoroscopic image data 52 includes the soft tissue 61 and a guide wire 63, and the blood vessel where the contrast agent does not exist is includes in the soft tissue 61. In the fluoroscopic image data, a part where the pixel value is large, that is, X-ray absorption is large, such as the blood vessel containing the contrast agent and the guide wire is displayed as dark color.

In a case where the fluoroscopic roadmap image data 53 obtained by subtracting the reference image data from the fluoroscopic image data, the blood vessel 62 of the reference image data 51 and the guide wire 63 of the fluoroscopic image data 52 are superimposed, for example. The operator inserts the guide wire, observing the position of the top of the guide wire and the blood vessel on the fluoroscopic roadmap image data.

Figure 8:
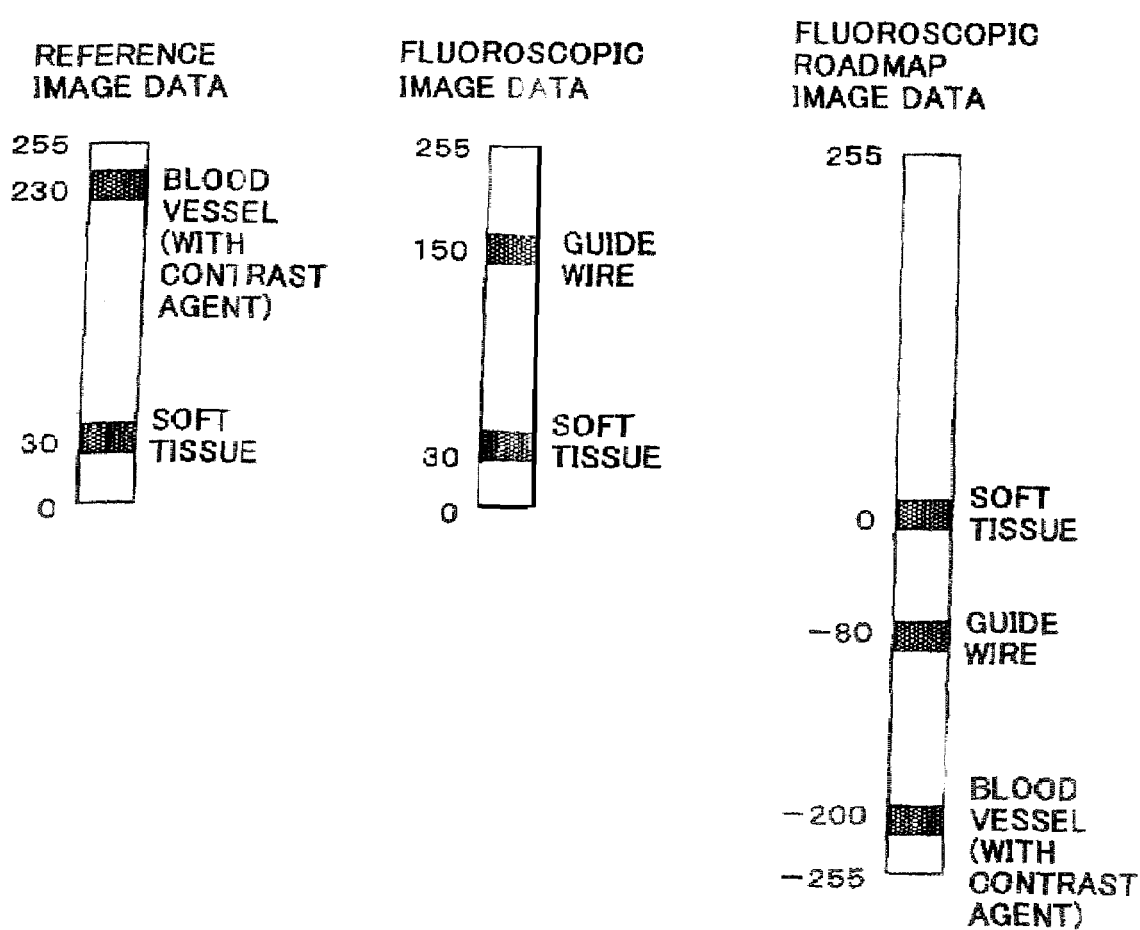
FIG. 8 is an illustration of pixel value of the fluoroscopic image data.

FIG. 8 shows an illustration for explaining brightness of pixel (pixel value) of the soft tissue 61, the blood vessel 62 during the contrast agent injection, the guide wire 63 on the reference image data, the fluoroscopic image data and the fluoroscopic roadmap image data. When white color (transmission 100%) is defined as 0 and block color (transmission 0%) is defined as 255, in the reference image data or the fluoroscopic image data, the pixel values of the soft tissue and the blood vessel which do not contain the contrast agent is 30, the pixel value of the blood vessel which contains the contrast agent is 230, and the pixel value of the guide wire is 150, for example. In the fluoroscopic roadmap image data which is a subtraction between the reference image data and the fluoroscopic image data, the pixel value of the soft tissue is 0, the pixel value of the blood vessel which contains the contrast agent is −200, and the pixel value of the guide wire is −80, for example. When the pixel value 0 is set as the block color and the pixel value −255 is set as the white color, it is possible to clearly distinguish the guide wire, the blood vessel and the soft tissue.

Observing the fluoroscopic roadmap image data displayed on the monitor 83 of the display unit 8, the operator changes the imaging direction for the fluoroscopic image data with the operation unit 9, when the fluoroscopic roadmap image data from another imaging direction is required (Step S18). From the changed imaging direction, the steps S14 to S17 are repeatedly performed, and the fluoroscopic roadmap image data from the changed imaging direction is displayed on the monitor 83 of the display unit 8.

The operator treats the patient 150 with the catheter if the information of the fluoroscopic roadmap image data is enough. After the treatment, the operator observes the fluoroscopic image data or the fluoroscopic roadmap image data obtained from at least one imaging direction, and confirms the result of the treatment. And then the X-ray imaging is completed (Step S19).

A modification of the first embodiment is explained referring to FIG. 1 through FIG. 9.

In the first embodiment, it is described that the contrast image data when the contrast agene is injected to the patient is used as the reference image data, however a case where the DSA image data is used as the reference image data in the modification.

Figure 9:
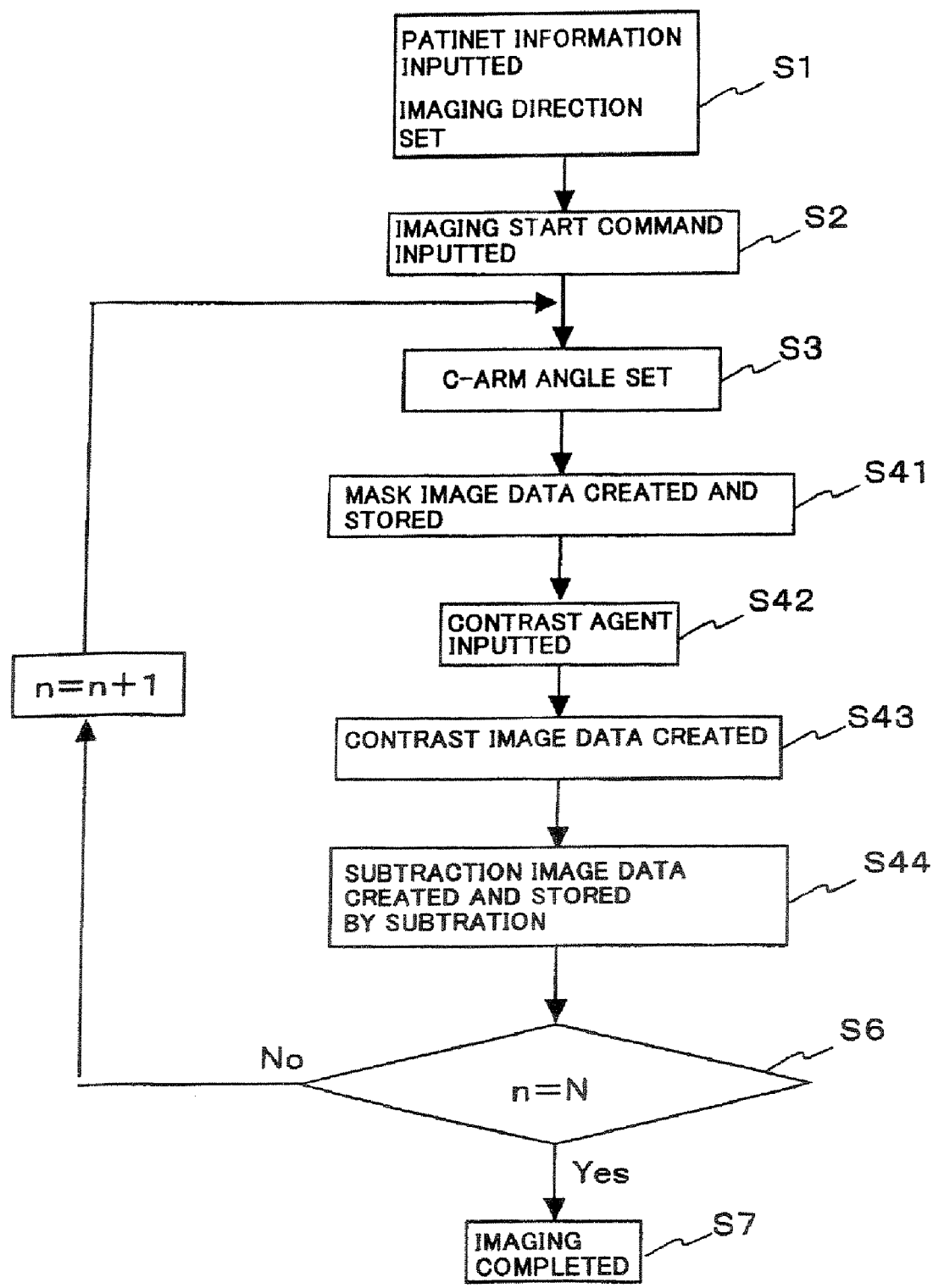
FIG. 9 is a flow chart for creating a reference image data of a modification of the first embodiment.

FIG. 9 is a flow chart for explaining an operation for creating the DSA image data as the reference image data. A detailed explanation is omitted to by attaching the same reference numbers on the same or the similar step in FIG. 4.

As well as the first embodiment, the patient information of the patient 150 and the imaging direction are set (Step S1), and the imaging start command for the reference image data is inputted (Step S2). The system control unit 10 which receives the command supplies the imaging condition to the C-arm/top plate moving controller 33. The C-arm/top plate moving controller 33 sets the C-arm angle based on the first imaging condition A-1 (n=1) such that the imaging direction of the X-ray irradiating unit 1 and the X-ray detecting unit 2 is 15 degrees in the LAO direction and 0 degree in the CRA direction (Step S3).

The system control unit 10 supplies a trigger signal for stating the imaging to the X-ray controller 41, and the X-ray controller 41 controls the high voltage generator 42 to supply the high voltage to the X-ray tube 15 which irradiates the X-ray to the patient. The X-ray passing through the patient is detected by the flat X-ray detector 21.

The two dimensional projection data is obtained by the projection data collecting unit 13 and the system control unit 10.

The image processing circuit 71 reads out the projection data from the image data memory circuit 72 and creates the mask image data by performing the image process. The mask image data is stored in the image data memory circuit 72 (Step S41).

The contrast agent is injected from the catheter inserted in the vein of the inguinal region of the patient (Step S42). The image processing circuit 71 creates the contrast image data after the contrast agent is injected from the same imaging direction as the direction of the mask image data in the same step for creating the mask image data (Step S43). The DSA image data is created by subtracting the mask image data which is read out from the image data memory circuit 72 from the contrast image data. The DSA image data is stored in the image data memory circuit 72 as the reference image data (Step S44).

After the reference image data is created in the first imaging condition A-1, the reference image data is created in the second imaging condition A-2 (n=2) trough A-N (n=N). The N sets of the reference image data are created and stored in the image data memory circuit 72, and the creation of the reference image data is completed (Step S7).

In the above modification, the mask image data is created before the contrast agent is injected into the patient 150, however the mask image data may be created after the contrast agent flows out enough.

In the first embodiment and the modification, when the fluoroscopic roadmap image data is displayed, even if the imaging direction is changed for the fluoroscopic image data, the corresponding reference image data to the fluoroscopic image data which is changed in the imaging direction can be selected among the sets of the reference image data. It is possible to observe and treat the diseased part continuously, which makes it easy to operation of the catheter. Thereby, safety and efficiency are improved in the diagnosis and the treatment.

Figure 10:
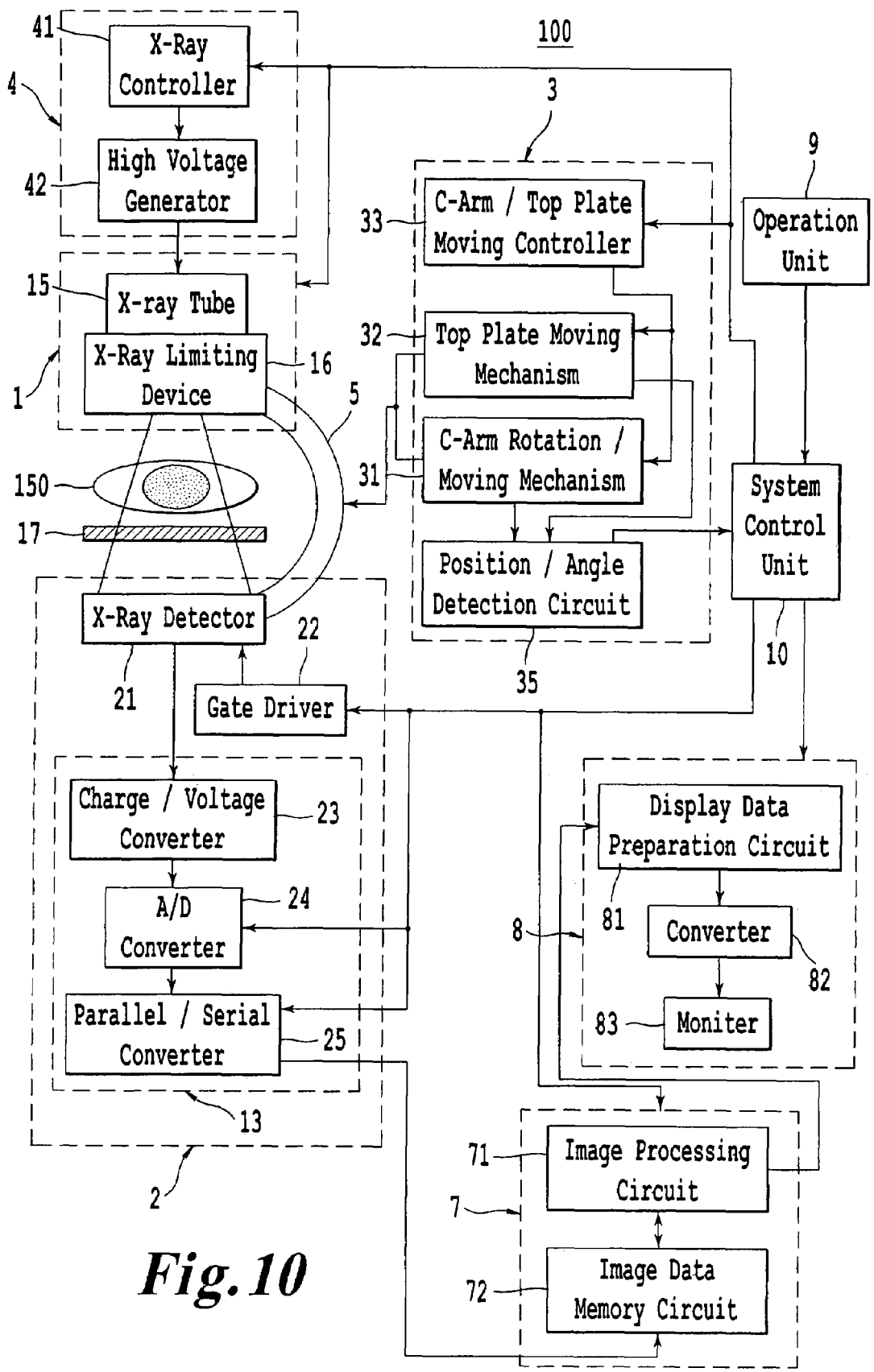
FIG. 10 is a block diagram of an X-ray diagnosis apparatus according to a second embodiment.
Figure 11:
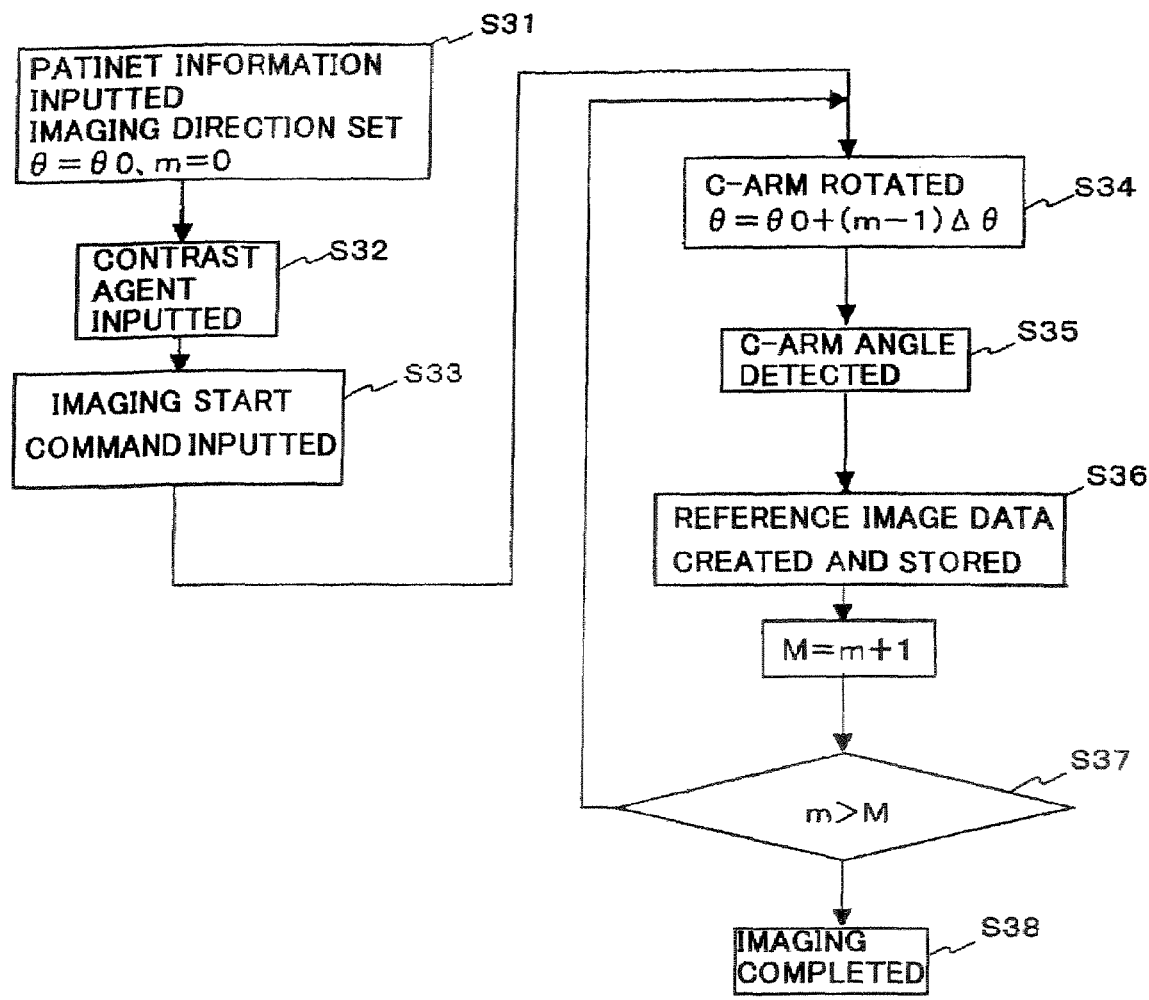
FIG. 11 is a flow chart for creating a reference image data of the second embodiment.
Figure 12:
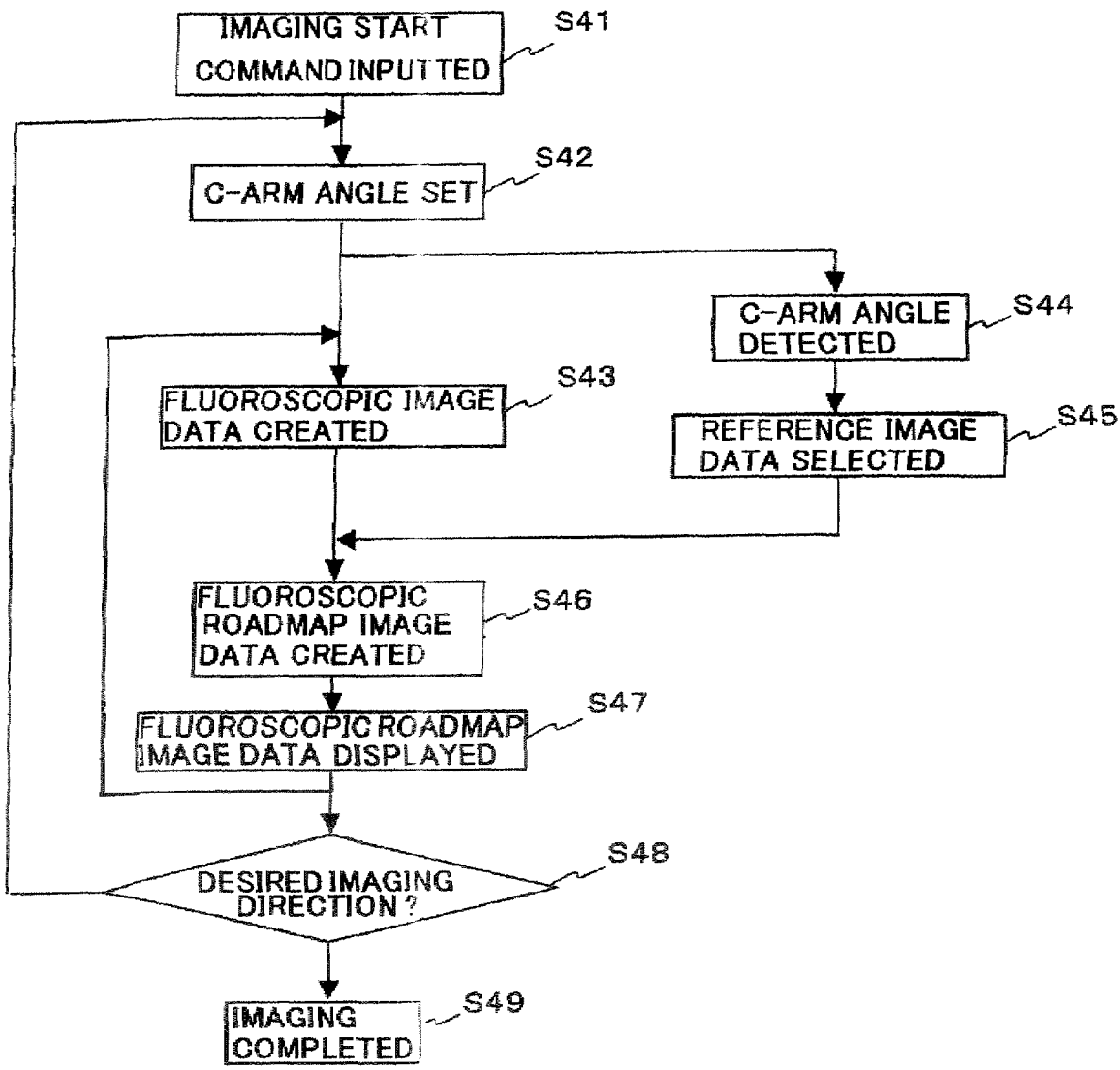
FIG. 12 is a flow chart for creating a fluoroscopic roadmap image data in the second embodiment.

A second embodiment is explained referring to FIG. 10 through FIG. 12. In the second embodiment which is different from the first embodiment, a plurality of sets of the reference image data are obtained by sequentially changing the imaging direction with a single injection of the contrast agent.

FIG. 10 is a block diagram of the X-ray diagnosis apparatus in the second embodiment. To simplify the explanation, the same or the similar constructions are omitted by attaching the same reference numbers.

The difference between FIG. 1 and FIG. 10 is that a position/angle detection circuit 35 which detects the rotation angel of the C-arm 5 and a position of the top plate 17 the is provided in a moving unit 3 in FIG. 10.

The image processing circuit 71 receives the imaging direction corresponding to the rotation angle detected by the position/angle detection circuit 35 via the system control unit 10. The fluoroscopic roadmap image data is created from the fluoroscopic image data which is obtained from the imaging direction and the reference image data which is selected from the sets of the reference image data.

An operation for creating the fluoroscopic roadmap image data in the X-ray diagnosis apparatus 100 in the embodiment, referring to FIG. 10 through FIG. 12.

The operator inputs the patient information and the imaging condition (Step S31). The contrast agent is injected into the blood vessel in the inguinal region of patient (Step S32). The start command is inputted for creating the reference image data (Step S33).

The system control unit 10 which receives the command sends a control signal to the C-arm rotation/moving mechanism 31 via the C-arm/top plate moving controller 33. The C-arm angle is set as an initial angle, and the X-ray imaging is performed by a $\Delta\theta$ step in the RAO-LAO direction or the CRA-CAU direction in order.

As well as the first embodiment, the system control unit 10 sets the angle of the C-arm 5 as the initial angle $\theta 0$ (Step S34), the position/angle detection circuit 35 detects the initial C-arm angle $\theta 0$, and stores the imaging direction corresponding to the initial C-arm angle $\theta 0$ in the image data memory circuit 72 with the reference image data (Step S35).

The system control unit 10 supplies a trigger signal for stating the imaging to the X-ray controller 41, and the X-ray controller 41 controls the high voltage generator 42 to supply the high voltage to the X-ray tube 15 which irradiates the X-ray to the patient. The X-ray passing through the patient is detected by the flat X-ray detector 21.

The two dimensional projection data is obtained by the projection data collecting unit 13 and the system control unit 10.

The image processing circuit 71 reads out the projection data from the image data memory circuit 72 and creates the reference image data. The reference image data is stored in the image data memory circuit 72 with the initial imaging direction (Step S36).

The C-arm 5 rotates by $\Delta\theta$ step from $\theta+\Delta\theta$ to $\theta+(M-1)\Delta\theta$ to create the reference image data, and the reference image data and the imaging data according to the rotation angle in the image data memory circuit 72 (Step S34 to S37). Thereafter, the X-ray imaging for the reference image data is completed (Step S38).

The operator inserts the catheter from the vein of the inguinal region such that the position of the top of the catheter reaches the coronary artery, and inputs an imaging start command for creating the fluoroscopic image data and the fluoroscopic roadmap image data with the operation unit 9 (Step S41).

The operator rotates the C-arm 5 to obtain the reference image data from a desired imaging direction, and the rotation angle is set according to the imaging direction (Step S42). The projection data and the fluoroscopic image data are created in the rotation angle (Step S43).

The position/angle detection circuit 35 detects the rotation angel of the C-arm 5 and the imaging direction is calculated according to the rotation angle (Step S44). The image processing circuit 71 reads out the reference image data of the imaging direction corresponding to the calculated imaging direction from the image data memory circuit 72 (Step S45). The fluoroscopic roadmap image data is created based on the reference image data and the fluoroscopic image data (Step S46). The fluoroscopic roadmap image data is stored in the image data memory circuit 72 and displayed on the monitor 83 of the display unit 8 (Step S47).

The operator executes the steps S43 through S47, proceeding the catheter, and the fluoroscopic roadmap image data from the desired imaging direction is displayed in real time.

The operator observes the fluoroscopic roadmap image data displayed on the monitor 83 of the display unit 8, and rotates the C-arm 6 to a desired direction with the operation unit 9, if necessary (Step S48) to change the imaging direction. From the change imaging direction, the steps S42 through S47 are executed repeatedly, and the fluoroscopic roadmap image data from the changed imaging direction is displayed in real time.

The operator confirms the result of the treatment with the fluoroscopic roadmap image data displayed in the display unit 8, and the X-ray imaging is completed (Step S49).

In the second embodiment, when the imaging direction is changed to a desired direction while the fluoroscopic roadmap image data is displayed, the reference image data from the same imaging direction as that of the changed fluoroscopic image data is selected among the sets of the reference image data. It is possible to observe and treat the diseased part continuously. Thereby, safety and efficiency are improved in the diagnosis and the treatment.

Moreover, in the second embodiment, the sets of the reference image data are obtained in a single injection of the contrast agent. Thereby, the time for creating the reference image data can be shortened and the burden of the patient can be reduced. In addition, the sets of the reference image data is obtained in the rotation direction, it is possible to accurately superimpose or separately display the reference image data and the fluoroscopic image data.

In the second embodiment, the DSA image data, namely rotation DSA image data, may be used as the reference image data as well as the first embodiment.

Figure 13:
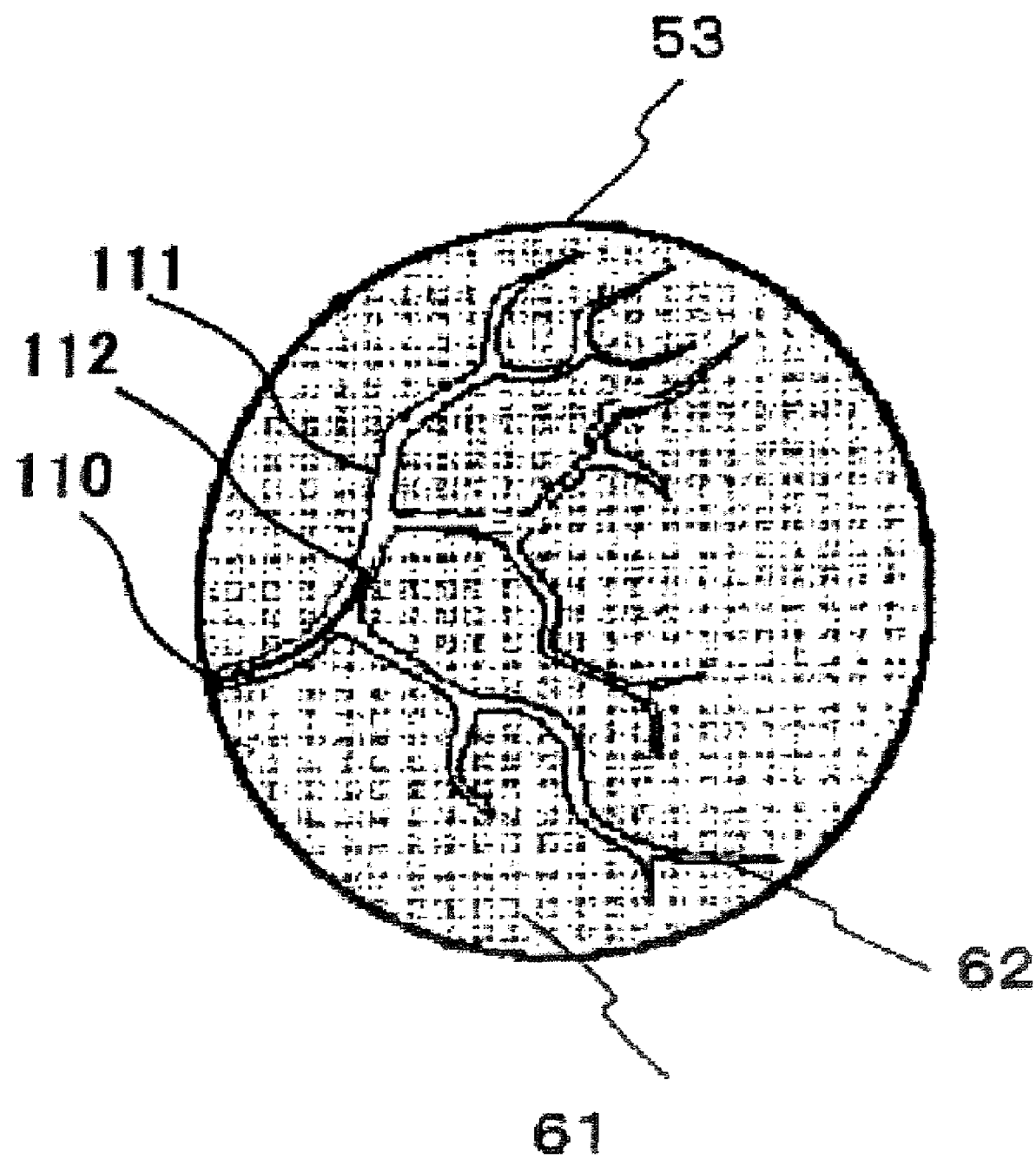
FIG. 13 is an illustration of fluoroscopic roadmap image data.

When the subtraction image data is applied as the fluoroscopic roadmap image data, the following new method may be used. The new method is that the fluoroscopic roadmap image data is made as if the contrast agent flowed. FIG. 13 is an illustration for explaining the hypothetical fluoroscopic roadmap image data. First, an end 110 of the catheter is detected in the displayed fluoroscopic roadmap image data. Since a shape of the catheter is apt to be rectangle on the subtraction image data, a point of the rectangle is detected. The detected point is inside of the blood vessel.

A region growing method is used from the detected point, and difference of pixel values is detected. Thereby, each pixel is classified as a blood vessel wall or not, a whole shape 111 of the blood vessel is identified. A top 112 of the catheter is detected in the identified blood vessel. Since the catheter is displayed as a while color in the fluoroscopic roadmap image data, a position of the top the catheter can be detected. When the catheter moves to an end of the blood vessel, the pixel value of the detected blood vessel is reversed from white color to a block color. According to a direction of the movement of the catheter, a symmetrical linear filter is applied. A filter condition of a length, a speed and a time interval where or when the symmetrical linear filter is used is set in advance. When a distance between the top of the catheter and a position where the symmetrical linear filter is sequentially changed to the direction of the movement of the catheter, the pixel values of the blood vessel is changed between the block and the white in order, which makes a hypothetical situation as if the contrast agent were injected. That is, even if the contrast agent is not injected, the blood vessel is displayed as if the operator injected the contrast agent. Moreover, a plurality of pixels may be grouped, and the pixel value may be changed by each group. The present invention may be not limited to the above embodiments, and various modifications may be made. For instance, a plurality of sets of the two dimensional image data are used as the reference image data in the above mentioned embodiments, however a three dimensional image data is used for creating the reference image data. In this case, the reference image data is created by projecting volume data of the three dimensional image data to a desired direction.

In the embodiments, the single C-arm is explained, however two or more C-arms, such as a biplane type, may be applied. In this case, the imaging direction is set by each C-arm.

The fluoroscopic roadmap image data may be created by performing an adding process or other processes of the reference image data and the fluoroscopic image data instead of the subtraction.

In FIG. 5, it is explained that the rotation angle of the C-arm is set, however a distance between the flat X-ray detector and the patient and an imaging range are set as parameter. Moreover, the flat X-ray detector is explained, however an I.I. and a CCD may be used.

What is claimed is:

1. An X-ray diagnosis apparatus, comprising:
   an X-ray generating unit configured to irradiate an X-ray to an object;
   an X-ray detector configured to detect the X-ray irradiated from the X-ray generating unit;
   a reference image data creation unit configured to create a plurality of sets of reference image data based on projection data obtained from a plurality of imaging directions to the object after a contrast agent is injected into the object;
   a fluoroscopic image data creation unit configured to create fluoroscopic image data based on projection data obtained from a desired imaging direction to the object; and
   a fluoroscopic roadmap image data creation unit configured to create fluoroscopic roadmap image data based on the fluoroscopic image data and one set of reference image data of the plurality of sets of reference image data whose imaging direction is closest to the imaging direction of the fluoroscopic image data, and
   wherein the reference image data creation unit creates DSA image data as the reference image data from mask image data that is obtained before the contrast agent is injected into the object and contrast image data that is obtained after the contrast agent is injected into the object.

2. The X-ray diagnosis apparatus according to claim 1, further comprising a direction set unit configured to set the plurality of imaging directions of the corresponding plurality of sets of the reference image data.

3. The X-ray diagnosis apparatus according to claim 2, wherein the direction set unit sets the plurality of imaging directions when an X-ray condition is initially set.

4. The X-ray diagnosis apparatus according to claim 2, wherein the direction set unit sets the plurality of imaging directions in at least one of an LAO-RAO direction and a CRA-CAU direction.

5. The X-ray diagnosis apparatus according to claim 2, wherein the direction set unit selects the imaging direction of the fluoroscopic image data from the imaging directions of the plurality of sets of the reference image data.

6. The X-ray diagnosis apparatus according to claim 2, wherein the direction set unit sets an imaging direction by rotating a support unit which supports the X-ray generating unit and the X-ray detector.

7. The X-ray diagnosis apparatus according to claim 1, further comprising a display unit configured to separately display or to superimpose the fluoroscopic image data and the fluoroscopic roadmap image data.

8. The X-ray diagnosis apparatus according to claim 1, wherein the fluoroscopic roadmap image data creation unit creates the fluoroscopic roadmap image data by performing a subtraction process on the reference image data and the fluoroscopic image data.

9. A method for creating image data in an X-ray diagnosis apparatus, comprising:
   creating a plurality of sets of reference image data based on projection data obtained from a plurality of imaging directions to an object after a contrast agent is injected into the object;
   creating fluoroscopic image data based on projection data obtained from a desired imaging direction to the object;
   creating fluoroscopic roadmap image data based on the fluoroscopic image data and one set of reference image data of the plurality of sets of reference image data whose imaging direction is closest to the imaging direction of the fluoroscopic image data; and displaying the fluoroscopic roadmap image data,
wherein the step of creating the plurality of sets of reference image data comprises creating DSA image data as the reference image data from mask image data that is obtained before the contrast agent is injected into the object and contrast image data that is obtained after the contrast agent is injected into the object.

10. The method for creating image data according to claim 9, further comprising the step of setting the plurality of imaging directions of the corresponding plurality of sets of the reference image data.

11. The method for creating image data according to claim 10, wherein the setting step comprises setting the plurality of imaging directions when an X-ray condition is initially set.

12. The method for creating image data according to claim 10, wherein the setting step comprises setting the plurality of imaging directions in at least one of an LAO-RAO direction and a CRA-CAU direction.

13. The method for creating image data according to claim 10, wherein the setting step comprises selecting the imaging direction of the fluoroscopic image data from the imaging directions of the plurality of sets of the reference image data.

14. The method for creating image data according to claim 10, wherein the setting step comprises setting an imaging direction by rotating a support unit which supports the X-ray generating unit and the X-ray detector.

15. The method for creating image data according to claim 9, further comprising separately displaying or superimposing the fluoroscopic image data and the fluoroscopic roadmap image data.

16. The method for creating image data according to claim 9, wherein the step of creating the fluoroscopic roadmap image data comprises creating the fluoroscopic roadmap image data by performing a subtraction process on the reference image data and the fluoroscopic image data.

* * * * *